(12) United States Patent
Khaderi

(10) Patent No.: US 7,938,539 B2
(45) Date of Patent: *May 10, 2011

(54) METHOD OF DEVELOPING A VISUAL PROCESSING PROFILE BASED ON A RETINO-GENICULO-CORTICAL PATHWAY

(76) Inventor: Syed Khizer Rahim Khaderi, Buena Park, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/577,109

(22) Filed: Oct. 9, 2009

(65) Prior Publication Data
US 2010/0045935 A1    Feb. 25, 2010

Related U.S. Application Data

(63) Continuation of application No. 11/867,477, filed on Oct. 4, 2007, now Pat. No. 7,621,639.

(60) Provisional application No. 60/849,313, filed on Oct. 4, 2006.

(51) Int. Cl.
*A61B 3/00* (2006.01)
*A61B 3/10* (2006.01)

(52) U.S. Cl. .................. 351/246; 351/205

(58) Field of Classification Search .......... 351/200–246
See application file for complete search history.

(56) References Cited

U.S. PATENT DOCUMENTS

| | | | |
|---|---|---|---|
| 4,408,846 A | 10/1983 | Balliet | 351/203 |
| 4,541,697 A | 9/1985 | Remijan | 351/211 |
| 4,726,672 A | 2/1988 | O'Brien et al. | 351/203 |
| 5,051,931 A | 9/1991 | Cheu et al. | 600/558 |
| 5,539,482 A | 7/1996 | James et al. | 351/246 |
| 6,464,356 B1 | 10/2002 | Sabel et al. | 351/203 |
| 6,916,096 B2 | 7/2005 | Eberl et al. | 351/209 |
| 7,004,912 B2 | 2/2006 | Polat et al. | 600/558 |
| 7,621,639 B2 * | 11/2009 | Khaderi | 351/246 |
| 2004/0049124 A1 | 3/2004 | Kullok et al. | 600/558 |
| 2005/0001980 A1 | 1/2005 | Spector | 351/246 |
| 2005/0153268 A1 | 7/2005 | Junkin et al. | 434/321 |
| 2006/0025658 A1 | 2/2006 | Newman et al. | 600/301 |
| 2006/0122886 A1 | 6/2006 | McKay | 705/14.64 |

(Continued)

FOREIGN PATENT DOCUMENTS
CA     2603583 A1     10/2006
(Continued)

OTHER PUBLICATIONS

"SITA Swap TM Software, A valuable new tool for the Humphrey Field Analyzer," Zeiss, 4 pages, Nov. 21, 2005.

(Continued)

*Primary Examiner* — Mohammed Hasan
(74) *Attorney, Agent, or Firm* — Morrison & Foerster LLP

(57) ABSTRACT

A method of developing a visual processing profile for a person including displaying a filtered visual stimuli to portions of the person's field of view; allowing the person to respond to the filtered visual stimuli; measuring the person's response to the filtered visual stimuli in the portions of the person's field of view; determining a level of retinal ganglion function of a first retinal ganglion subtype for the person based on at least the person's measured response to the filtered visual stimuli; determining a level of retinal ganglion function for at least a second retinal ganglion subtype; and determining the visual processing profile for the person based on at least the determined levels of retinal ganglion function for at least the first and second retinal ganglion subtypes.

17 Claims, 8 Drawing Sheets

U.S. PATENT DOCUMENTS

| | | | |
|---|---|---|---|
| 2007/0076168 A1 | 4/2007 | Ellenbogen | 351/243 |
| 2007/0091265 A1* | 4/2007 | Kardon et al. | 351/206 |
| 2007/0182928 A1 | 8/2007 | Sabel | 351/206 |
| 2007/0216865 A1 | 9/2007 | Sabel et al. | 351/203 |
| 2008/0013047 A1 | 1/2008 | Todd et al. | 351/222 |
| 2008/0024724 A1 | 1/2008 | Todd | 351/222 |
| 2008/0024725 A1 | 1/2008 | Todd | 351/222 |
| 2008/0043201 A1 | 2/2008 | Todd | 351/222 |
| 2008/0077437 A1 | 3/2008 | Mehta et al. | 351/222 |

FOREIGN PATENT DOCUMENTS

| | | |
|---|---|---|
| JP | 2007-216051 A | 8/2007 |
| WO | WO-01/47463 A1 | 7/2001 |
| WO | WO-2005/044096 A2 | 5/2005 |
| WO | WO-2007/043047 A2 | 4/2007 |
| WO | WO-2007/090163 A1 | 8/2007 |
| WO | WO-2007/109724 A1 | 9/2007 |

OTHER PUBLICATIONS

"The Most Amazing Inventions," *Time*, Nov. 21, 2005, 1 page.

Abernethy et al. (1999). "Visual Characteristics of Clay Target Shooters," *Journal of Science and Medicine in Sport* 2 1:1-19.

Altersitz, (Apr. 1, 2006). "Refractive surgery, Low-tech test is effective for determining eye dominance," OSN SuperSite, www.osnsupersite.com, 3 pages.

Alvarez et al. (1997). "Comparison of Red-Green, Blue-Yellow and Achromatic Losses in Glaucoma" *Vision Research* 37(16):2295-2301.

Beckerman et al. (Aug. 2003). "Sports vision testing of selected athletic participants in the 1997 and 1998 AAU Junior Olympic Games," *Optometry* 74(8):502-514.

Bengtsson et al. (Nov. 2003). "Normal Intersubject Threshold Variability and Normal Limits of the SITA SWAP and Full Threshold SWAP Perimetric Programs," *Investigative Ophthalmology & Visual Science* 44(11):5029-5034.

Bengtsson, (Mar. 2003). "A New Rapid Threshold Algorithm for Short-Wavelength Automated Perimetry," *Investigative Ophthalmology & Visual Science* 44(3):1388-1394.

Castel et al. (2005). "The effects of action video game experience on the time course of inhibition of return and the efficiency of visual search," *Acta Psychologica* 119:217-230.

Cavanagh et al. (Jul. 2005). "Tracking multiple targets with multifocal attention," *TRENDS in Cognitive Sciences* 9(7):349-354.

Cello et al. (Mar. 2000). "Frequency Doubling Technology Perimetry for Detection of Glaucomatous Visual Field Loss," *American Journal of Ophthalmology* 129(3):314-322.

Chauhan et al. (Jan. 1999). "Comparison of Conventional and High-Pass Resolution Perimetry in a Prospective Study of Patients with Glaucoma and Healthy Controls," *Archives of Ophthalmology* 117:24-33.

Chauhan et al. (Mar. 1999). "Test-Retest Variability of Frequency-Doubling Perimetry and Conventional Perimetry in Glaucoma Patients and Normal Subjects," *Investigative Ophthalmology & Visual Science* 40(3):648-656.

Culham et al. (1998). "Cortical fMRI Activation Produced by Attentive Tracking of Moving Targets," *The American Physiological Society* 2657-2670.

Donahue (1999). "Perimetry techniques in neuro-ophthalmology," *Current Opinion in Ophthalmology* 10:420-428.

Ehrlich, (2005). "The human brain's algorithm for extrapolating motion, and its possible gender-dependence," *Neuroscience Letters* 374:38-42.

Green et al. (May 2003). "Action video game modifies visual selective attention," *Nature* 423(29):534-537.

Greenstein et al. (1996). "Chromatic and Luminance Systems Deficits in Glaucoma," *Vision Research* 36(4):621-629.

Heeg et al. (2003). "Learning effect, normal range, and test-retest variability of Frequency Doubling Perimetry as a function of age, perimetric experience, and the presence or absence of glaucoma," *Ophthalmic and Physiological Optics* 23(6):535-540.

Hofeldt et al. (Dec. 1996). "Baseball Hitting, Binocular Vision, and the Pulfrich Phenomenon," *Archives of Ophthalmology* 114:1490-1494.

Hofeldt et al. (1993). "Stereophotometric Testing for Pulfrich's Phenomenon in Professional Baseball Players," *Perceptual and Motor Skills* 77:407-416.

Hoyt (Jun. 2004). "Delayed Visual Maturation: The Apparently Blind Infant," *Journal of AAPOS* 8(3):215-219.

International Search Report for Application No. PCT/07/080458 dated Apr. 11, 2008.

International Search Report for International Patent Application No. PCT/US07/80462 dated Oct. 28, 2008.

Johnson et al. "A Primer for Frequency Doubling Technology," Humphrey Systems, 63 pages.

Kaplan et al. (Apr. 1986). "The primate retina contains two types of ganglion cells, with high and low contrast sensitivity," *Proceedings of the National Academy of Sciences USA* 83:2755-2757.

Kluka et al. (Mar. 1993). "The effects of daily-wear contact lenses on contrast sensitivity in selected professional and collegiate female tennis players," *Journal of the American Optometric Association* 64(3):182-186.

Laby et al. (Oct. 1996). "The Visual Function of Professional Baseball Players," *American Journal of Ophthalmology* 122(4):476-485.

Maddess et al. (1999). "Testing for glaucoma with the spatial frequency doubling illusion," *Vision Research* 39:4258-4273.

McKendrick et al. (Jun. 2004). "Psychophysical Measurement of Neural Adaptation Abnormalities in Magnocellular and Parvocellular Pathways in Glaucoma," *Investigative Ophthalmology & Visual Science* 45(6):1846-1853.

Melcher et al. (Jul. 1992). "Sports Vision and High School Student Athlete," *Journal of the American Optometric Association* 63(7):466-474.

Muskens et al. (2004). "An evaluation of algorithms designed to classify the results from frequency doubling perimetry," *Ophthalmic and Physiological Optics* 24(6):498-503.

Oksama et al. (2004). "Is multiple object tracking carried out automatically by an early vision mechanism independent of higher-order cognition? An individual difference approach," *Visual Cognition* 11(5):631-671.

Portal et al. (Sep. 8, 1998). "Ocular Sighting Dominance: A Review and a Study of Athletic Proficiency and Eye-Hand Dominance in a Collegiate Baseball Team," *New England Journal of Medicine* 319(10):125-132.

Schiller et al. (Aug. 1986). "Functions of the ON and OFF channels of the visual system," *Nature* 322(28):824-825.

Schwarz, "Swing Batter Batter," 1 page.

Steinberg et al. (1995). "Dextrality and Eye Position in Putting Performance," *Perceptual and Motor Skills* 80:635-640.

\* cited by examiner

METHOD OF DEVELOPING A VISUAL PROCESSING PROFILE BASED ON A RETINO-GENICULO-CORTICAL PATHWAY

CROSS-REFERENCE TO RELATED APPLICATIONS

This application is a Continuation of U.S. patent application Ser. No. 11/867,477, with a filing date of Oct. 4, 2007, U.S. Pat. No. 7,621,639 B2 which claims the benefit of U.S. Provisional Application Ser. No. 60/849,313, with a filing date of Oct. 4, 2006, all of which are hereby incorporated by reference in the present disclosure in their entirety.

TECHNICAL FIELD

The following disclosure relates to a system and method of developing a visual processing profile based on a retino-geniculo-cortical pathway.

BACKGROUND

The structures of the human eye transmit an image to the retina based on photons absorbed from the visual field. The retina contains five different cell types, organized in laminar fashion. At the back of the retina, furthest from the cornea, are a plurality of photoreceptors that convert light into electrochemical signals. Photoreceptors exist in two varieties: rod photoreceptors and cone photoreceptors. Rod photoreceptors have a long, cylindrically shaped outer segment with membranous disks that are stacked with photopigment. Cone cells have a shorter, more tapered outer segment with fewer membranous disks. The rods are much more sensitive to light than cones and mediate most vision at night or in low light. In contrast, the cones are differentially sensitive to varying wavelengths, and mediate color vision.

The electrochemical signals are relayed from the photoreceptors through the bipolar cells to the ganglion cells. The ganglion cells gather information and send it to the brain through the optic nerve. The innermost layer is the ganglion cell layer, which is the location of the ganglion cell bodies. The inner nuclear layer contains the cell bodies of the bipolar, amacrine and horizontal cells and the outer nuclear layer contains the cell bodies of the photoreceptors. The inner plexiform layer contains the connections between the bipolar, amacrine and ganglion cells. The outer plexiform layer contains the connections between the photoreceptors, horizontal cells and bipolar cells. The outer segments of the photoreceptor cells border on the pigmented epithelium, which absorbs excess light at the back of the retina.

Just like the rods and cones, whose stricture and function are oriented entirely toward converting light energy into nerve impulses, every other type of cell in the retina is located and connected to perform some initial step in the processing of visual information.

While the other neurons in the retina emit only graduated electrical potentials, the ganglion cells are the only ones that send out neural signals in the form of action potentials. When it is considered that it is the ganglion cells' axons that form the optic nerve and thereby transmit information from the retina over large distances, the significance of the generation of action potentials in these cells becomes apparent. These potentials are generated spontaneously; and it is the frequency at which they are discharged that is increased or decreased by the appearance of light in these cells' receptive fields.

Though most ganglion cells have either ON-centre OFF-surround receptive fields or the reverse, there are other criteria that define other categories. On the basis of overall appearance, neural connections, and electrophysiological traits, at least three such categories of ganglion cells have been distinguished in retinas. However it is believed that at least eighteen different categories of ganglion cells exist in a human retina.

Intermediate cells such as bipolar cells, amacrine cells and horizontal cells convey the information received by the photoreceptors to neurons called ganglion cells. The human eye contains about 1.2 to 1.5 million retinal ganglion cells. As discussed above, there are three major types (subtypes) or categories of ganglion cells classified by their structure and function. These cells, the magnocellular cells (m-cells), parvocellular cells (p-cells) and koniocellular cells (k-cells) each having a unique role in visual processing.

The small parvocellular (or "p-cells") ganglion cells (from the Latin parvus, meaning "small") represent about 90% of the total population of ganglion cells. Large magnocellular (or "m-type") ganglion cells (from the Latin magnus, meaning "large") account for about 5%. Non-m, non-p ganglion cells, which have not yet been well characterized, account for the remaining 5%. These non-m, non-p cells include k-cells.

M-cells receive signals from a large number of photoreceptor cells. They have fast conduction velocities resulting in quick propagation of nerve impulses over a relatively large receptive field. The m-cells process images with low spatial resolution, but a fast temporal resolution. Furthermore, the m-cells demonstrate association with regions of the brain responsible for motion perception. Although these cells are sensitive to contrast stimulus, they show only weak response to chromatic input.

In contrast, the p-cells are responsible for the processing and visualization of color stimulus. They are generally involved in processing images at a lower conduction velocity and have a smaller receptive field responding to a small number of photoreceptor cells. Particularly, the p-cells show red-green color opponency having responses consistent with the interaction between medium-wavelength-sensitive (M or "green") and long-wavelength-sensitive (L or "red") photoreceptor cone cells. The p-cells show sustained response to stimuli and, opposite the m-cells, process images with high spatial resolution and slowed temporal resolution. The p-cells show association with areas of the brain relating to visual acuity and color perception.

The most commonly accepted theory is that m-cells are particularly involved in detecting movement in a stimulus, whereas p-cells, with their small receptive fields, would be more sensitive to its shape and details.

Cells belonging to the koniocellular ganglion pathway have a large visual field and show blue-yellow color opponency. K-cells show responses consistent with excitation from the short-wavelength-sensitive (S or "blue") and opponent input from a mixture of M and L cones. These "blue-on" cells are thought to derive opponent cone inputs through depolarizing and hyperpolarizing pathways.

Another distinction is essential for color detection: most p-cells and some non-m non-p cells are sensitive to differences in the wavelengths of light. Most p-cells are in fact "single color opponent cells," which means that the response to a given wavelength at the centre of their receptive fields is inhibited by the response to another wavelength in the surround. In the case of a cell with a red ON-centre and a green OFF-surround, red cones occupy the centre of the field and green cones occupy the surround. The same thing goes for cells with blue-yellow opposition, in which blue cones are opposed to red and green ones. Type M ganglion cells do not have any color opposition, simply because both the centre and the surround simultaneously receive information from more than one type of cone. Also, there are no m-cells in the fovea, which confirms that these cells do not play a role in processing color.

Various methods for determining the function of specific retinal ganglion cell types are known in the art. Current diagnostic tools and methods center on comparison of an individual to population norms to identify disease processes and stabilizing visual acuity based on these norms as well as coordination and timing of vision with bodily movements. However, these diagnostics and methods fail to address the visual processing of an individual as a ratio of retinal ganglion cell function. Furthermore, a correlation between the ratio or level of retinal ganglion function and high visual performance has not been thoroughly explained. Thus, there is a need in the art to determine and alter the ratio of function in the various retinal ganglion cells.

SUMMARY

The present disclosure is directed to a method of developing a visual processing profile for a person including displaying a filtered visual stimuli to portions of the person's field of view; allowing the person to respond to the filtered visual stimuli; measuring the person's response to the filtered visual stimuli in the portions of the person's field of view; determining a level of retinal ganglion function of a first retinal ganglion subtype for the person based on at least the person's measured response to the filtered visual stimuli; determining a level of retinal ganglion function for at least a second retinal ganglion subtype; and determining the visual processing profile for the person based on at least the determined levels of retinal ganglion function for at least the first and second retinal ganglion subtypes.

In another aspect, the disclosure is directed to a method of developing a visual processing profile for a person that includes displaying a first filtered visual stimulus to a first portion of the person's field of view using a neutral density filter; allowing the person to respond to the first filtered visual stimulus; measuring the person's response to the first filtered visual stimulus in the first portion of the person's field of view; and displaying a second filtered visual stimulus to a second portion of the person's field of view. The method further includes allowing the person to respond to the second filtered visual stimulus; measuring the person's response to the second filtered visual stimulus in the second portion of the person's field of view; displaying a third filtered visual stimulus to the first portion of the field of View using a second, darker neutral density filter; allowing the person to respond to the third filtered visual stimulus; measuring the person's response to the third filtered visual stimulus in the first portion of the person's field of view; displaying a fourth filtered visual stimulus to the second portion of the person's field of view using the second, darker neutral density filter; allowing the person to respond to the fourth filtered visual stimulus; and measuring the person's response to the fourth filtered visual stimulus in the peripheral portion of the person's field of view;

The method also includes determining the level of retinal ganglion function of the plurality of magnocellular cells based on at least the person's measured responses to at least the first, second, third, and fourth filtered visual stimuli; determining the level of retinal ganglion function for the plurality of non-magnocellular cells; determining the visual processing profile for the person based on a ratio of the determined levels of retinal ganglion function for at least the plurality of magnocellular cells and the plurality of non-magnocellular cells; and comparing the determined visual processing profile for the person to a predetermined visual processing profile to determine a variance from the predetermined visual processing profile.

The present disclosure is also directed to a method of developing a visual processing profile for a person including determining a level of retinal ganglion function of a first retinal ganglion subtype for the person; determining a level of retinal ganglion function for at least a second retinal ganglion subtype; determining the visual processing profile for the person based on at least the determined levels of retinal ganglion function for at least the first and second retinal ganglion subtypes; and comparing the determined visual processing profile for the person to a predetermined visual processing profile to determine a variance from the predetermined visual processing profile.

DETAILED DESCRIPTION

The present disclosure describes a method of developing a visual processing profile for a person. The method may be performed on a single system that incorporates a number of separate components or on a distributed system which separates a portion of the measuring, computing, and storing components across a network. One example of such a network is described below.

Figure 1:
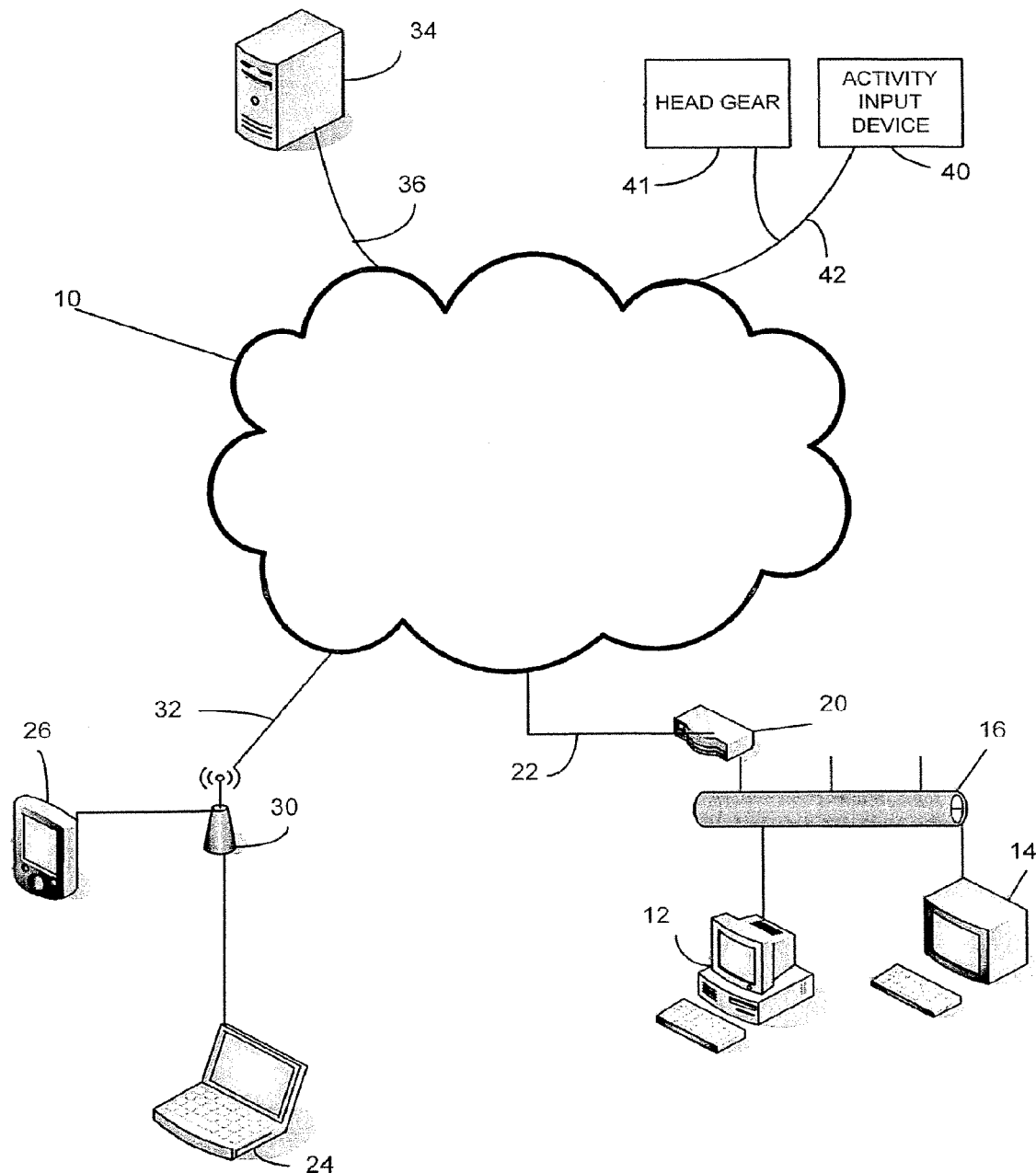
FIG. 1 is a diagram of one example of a network and network devices.

FIG. 1 illustrates an example of a network typical of the World Wide Web. A network 10 may be a virtual private network (VPN), or any other network that allows one or more computers, communication devices, databases, etc., to be communicatively connected to each other. The network 10 may be connected to a PC 12 and a computer terminal and monitor 14 via an Ethernet 16 and a router 20, and a land line 22. The network 10 may also be wirelessly connected to a laptop computer 24 and a personal data assistant 26 via a wireless communication station 30 and a wireless link 32. Similarly, a server 34 may be connected to the network 10 using a communication link 36.

Also, an activity input device 40 for measuring motion associated with physical activity of a user and a headset 41 for generating images and/or sounds for the user may be connected to the network 10 using another communication link 42. These components may alternatively be coupled to the network 10 via the wireless communication station 30 and the wireless link 32. Where the network 10 includes the Internet, data communication may take place over the network 10 via an Internet communication protocol. In operation, the client PC 12 may view or request data from any other computing device connected to the network 10. Further, the PC 12 may send data to any other computing device connected to the network 10. It is noted that each of the components listed above may be general purpose components or specially designed components for developing a visual processing profile for a person and enhancing a retino-geniculo-cortical pathway for the person.

Figure 2:
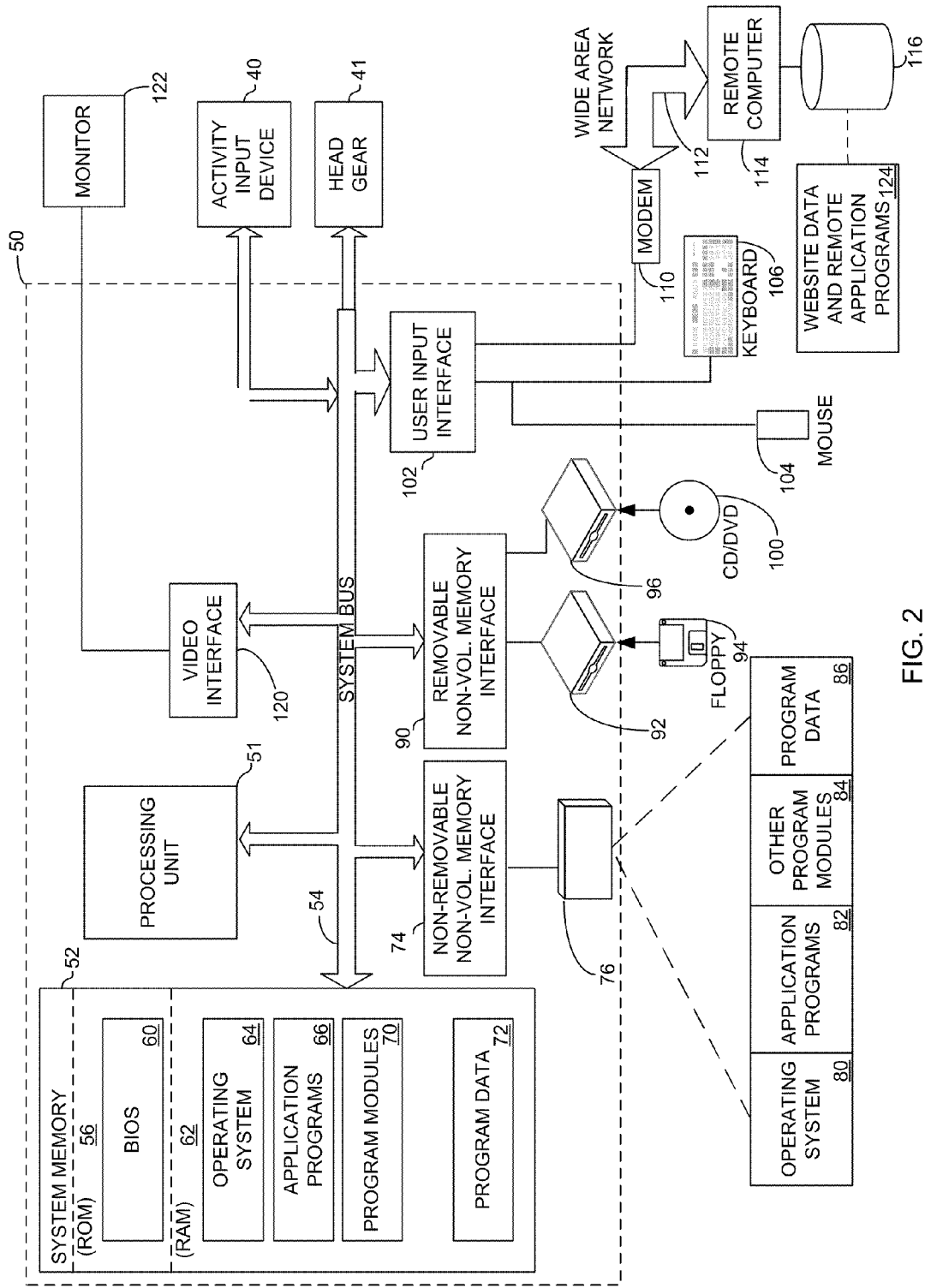
FIG. 2 is a diagram of one example of a general computing device that may operate in accordance with the claims.

FIG. 2 illustrates a typical computing device 50 that may be connected to the network 10 of FIG. 1 and participate in a measuring and computing environment such as the World Wide Web. FIG. 2 may also be an example of an appropriate computing system on which the claimed apparatus and claims may be implemented, however, FIG. 2 is only one example of a suitable computing system and is not intended to limit the scope or function of any claim. The claims are operational with many other general or special purpose computing devices such as PCs 12, server computers 34, portable computing devices such as a laptop 24, consumer electronics 26, wired and wireless activity input devices 40, wired and wireless head gear 41, mainframe computers, or distributed computing environments that include any of the above or similar systems or devices.

With reference to FIG. 2, a system for implementing the steps of the claimed apparatus may include several general computing devices in the form of a computer 50. The computer 50 may include a processing unit, 51, a system memory, 52, and a system bus 54 that couples various system components including the system memory 52 to the processing unit 51. The system bus 54 may include an Industry Standard Architecture (ISA) bus, a Micro Channel Architecture (MCA) bus, Enhanced ISA (EISA) bus, Video Electronics Standards Association (VESA) local bus, a Peripheral Component Interconnect (PCI) bus or a Mezzanine bus, and the Peripheral Component Interconnect Express (PCI-E) bus.

The computer 50 may include an assortment of computer-readable media. Computer-readable media may be any media that may be accessed by the computer 50. By way of example, and not limitation, the media may include both volatile and nonvolatile media, removable and non-removable media. Media may also include computer storage media and communication media. Computer storage media may include volatile and nonvolatile, removable and non-removable media that stores information such as computer-readable instructions, program modules, data structures, or other data. Computer-storage media may include RAM, ROM, EEPROM, or other memory technology, optical storage disks, magnetic storage devices, and any other medium which may be used to store computer-accessible information. Communication media may be computer-readable instructions, data structures, program modules, or other data in a modulated data signal or other transport mechanism. Communication media may include wired media such as a wired network or direct-wired connection, and wireless media such as RF, infrared, and other wireless media.

The system memory 52 may include storage media in the form of volatile and/or non-volatile memory such as ROM 56 and RAM 62. A basic input/output system 60 (BIOS), containing algorithms to transfer information between components within the computer 50, may be stored in ROM 56. Data or program modules that are immediately accessible or are presently in use by the processing unit 51 may be stored in RAM 62. Data normally stored in RAM while the computer 50 is in operation may include an operating system 64, application programs 66, program modules 70, and program data 72.

The computer 50 may also include other storage media such as a hard disk drive 76 that may read from or write to non-removable, non-volatile magnetic media, a magnetic disk drive 251 that reads from or writes to a removable, non-volatile magnetic disk 94, and an optical disk drive 96 that reads from or writes to a removable, nonvolatile optical disk 100. Other storage media that may be used includes magnetic tape cassettes, flash memory cards, digital versatile disks, digital video tape, solid state RAM, and solid state ROM. The hard disk drive 76 may be connected to the system bus 54 through a non-removable memory interface such as interface 74. A magnetic disk drive 92 and optical disk drive 96 may be connected to the system bus 54 by a removable memory interface, such as interface 90.

The disk drives 92, 96 transfer computer-readable instructions, data structures, program modules, and other data for the computer 50 to different storage media 94, 100 for storage. A hard disk drive 76 may store an operating system 64, application programs 66, other program modules 70, and program data 72. These components may be the same or different from operating system 64, application programs 66, other program modules 70 and program data 72. The components associated with the hard disk drive 76 may be different copies than those associated with RAM 62.

The user may interact with the computer 50 through input devices such as a keyboard 106, a pointing device 104 (i.e., a mouse), an activity input device 40, or head gear 41. A user input interface 102 may be coupled to the system bus 54 to allow the input devices to communicate with the processing unit 51. A display device such as a monitor 122 may also be connected to the system bus 54 via a video interface 120.

The computer 50 may operate in a networked environment using logical connections to one or more remote computers 114. The remote computer 114 may be a PC 12, a server 34, a router 20, or other common network node as illustrated in FIG. 1. The remote computer 114 typically includes many or all of the previously-described elements regarding the computer 50, even though only a memory storage device 116 is illustrated in FIG. 2. Logical connections between the computer 50 and one or more remote computers 114 may include a wide area network (WAN) 112. A typical WAN is the Internet. When used in a WAN, the computer 50 may include a modem 110 or other means for establishing communications over the WAN. The modem 110 may be connected to the system bus 54 via the user input interface 102, or other mechanism. In a networked environment, program modules depicted relative to the computer 50, may be stored in the remote memory storage device 116. By way of example, and not limitation, FIG. 2 illustrates website data and remote application programs 124 as residing on the memory device 116. As may be appreciated, other means of establishing a communications link between the computer 50 and the remote computer 114 may be used.

In accordance with the present disclosure, a system and method for altering vision are provided. In particular, the disclosure relates to a system and method of stimulating the retinal ganglion pathways, thereby influencing visual processing and the overall retino-geniculo-cortical pathway. The level and/or type of stimulation may be adjusted according to the visual profile of the individual.

A level of function in retinal ganglion cell types may be assessed to determine a visual processing profile and to identify a need for alteration in one or more subtype of ganglion cells. Generally, three types of major retinal ganglion subtypes are evaluated in the assessment step. Such retinal ganglion cell types may include m-cells, p-cells and k-cells cells. However, fewer or greater types of retinal ganglion subtypes may be evaluated such as, for example, m-cells and non m-cells. The assessment of a functional level in any one of the retinal ganglion cell types is useful in the determination of visual stimulus.

The visual processing profile may be determined using a number of methods known in the art. In certain aspects, the visual profile may include a level of function of the retinal-geniculo-cortical pathway, and in particular, the retinal ganglion cells. Such levels may be based on criteria such as the conduction velocity of the retinal cells. A number of methods known in the art may be used in the determination of retinal ganglion function. For example, steady-state pattern electroretinogram (PERG), optical coherence tomography (OCT), visual function-specific field tests, frequency doubling technology (FDT), Snellen test, contrast sensitivity testing, high-pass resolution perimetry (HRP), short-wavelength automated perimetry (SWAP) and visually evoked potentials (VEP), and multi-focal visually evoked potentials (EVEP) are among the various method useful in assessing visual function associated with the retinal ganglion subtypes. Furthermore, retinal ganglion cell function may be determined by any means developed to stress the specific visual functions associated with each ganglion subtype as described above.

Figure 3A:
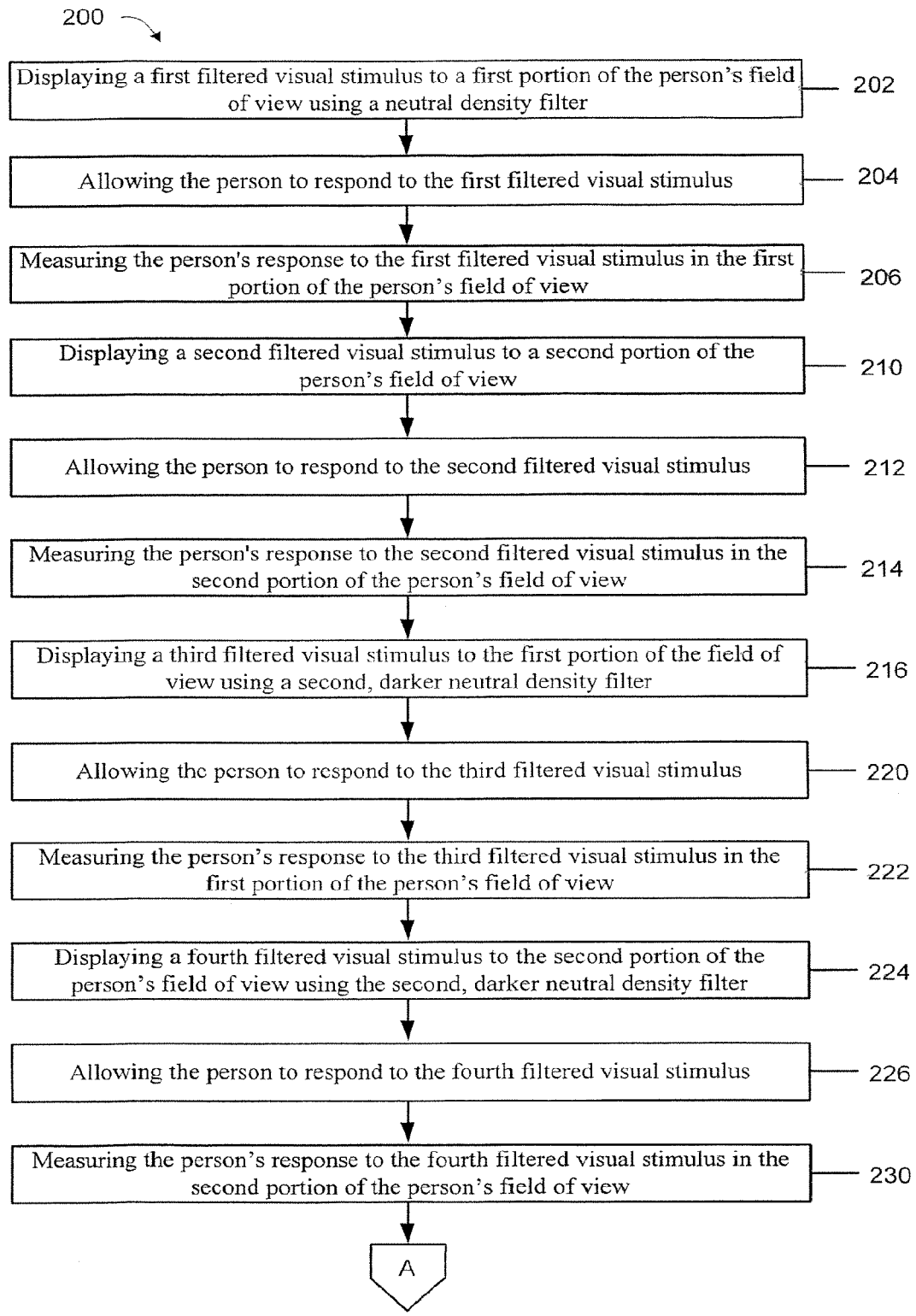
FIGS. 3A and 3B are two parts of a flowchart describing a method of one example of developing a visual processing profile.
Figure 3B:
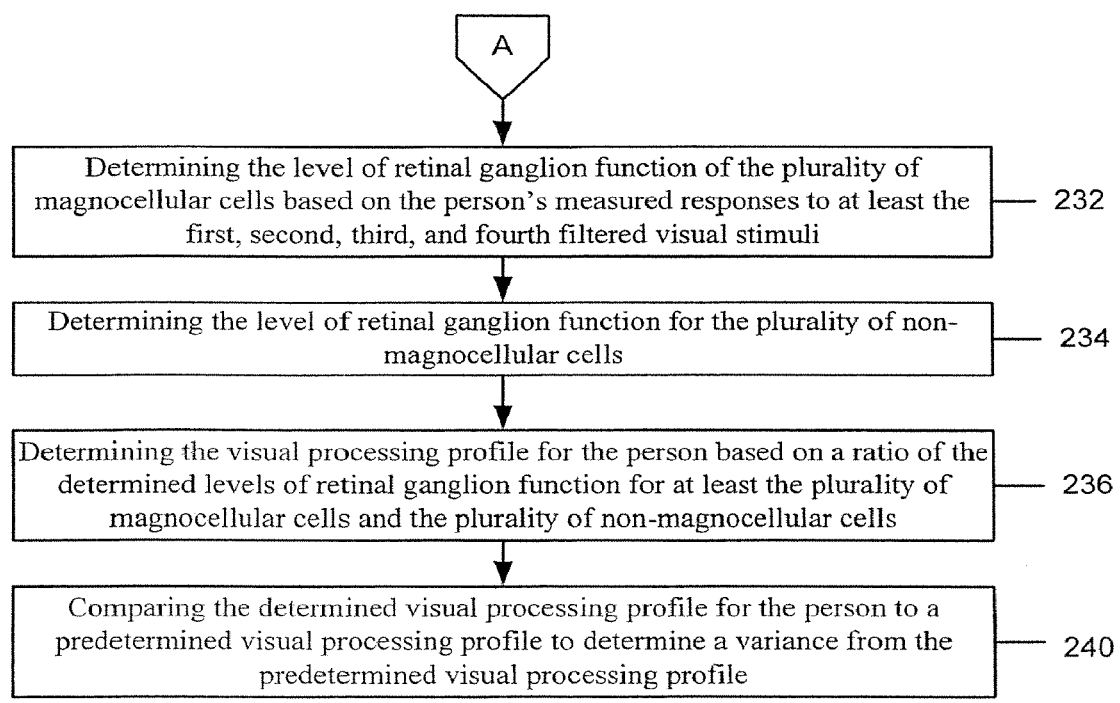

FIGS. 3A and 3B are two parts of an exemplary method 200 of developing a visual processing profile for a person. The method 200 may begin by displaying a first filtered visual stimulus to a first portion of the person's field of view using a neutral density filter (block 202). The visual stimulus could thus be displayed to various portions of the person's field of view, such as, for example, a central portion or a peripheral portion; or within one of those portions, a superior portion, a nasal portion, an inferior portion, a temporal portion, or the entire visual field, etc. The method 200 may then allow the person to respond to the first filtered visual stimulus (block 204). The method may then measure the person's response to the first filtered visual stimulus in the first portion of the person's field of view (block 206).

The method 200 may then display a second filtered visual stimulus to a second portion of the person's field of view (block 210) and allow the person to respond to the second filtered visual stimulus (block 212). The method may then measure the person's response to the second filtered visual stimulus in the peripheral portion of the person's field of view (block 214). The method 200 may then display a third filtered visual stimulus to the first portion of the field of view using a second, darker neutral density filter (block 216) and then allow the person to respond to the third filtered visual stimulus (block 220). The method may also include measuring the person's response to the third filtered visual stimulus in the first portion of the person's field of view (block 222).

After measuring the person's response to the third filtered visual stimulus, the method 200 may display a fourth filtered visual stimulus to the second portion of the person's field of view using the second, darker neutral density filter (block 224) and allow the person to respond to the fourth filtered visual stimulus (block 226). The method 200 may then measure the person's response to the fourth filtered visual stimulus in the second portion of the person's field of view (block 230).

Continuing to FIG. 3B, the method 200 may determine the level of retinal ganglion function of the plurality of magnocellular cells based on at least the person's measured responses to at least the first, second, third, and a fourth filtered visual stimuli (block 232) and determine the level of retinal ganglion function for the plurality of non-magnocellular cells (block 234). This could include the person's p-cells and k-cells, as well as any other subtypes of ganglion cells.

The method 200 may then determined the visual processing profile for the person based on a ratio of the determined levels of retinal ganglion function for at least the plurality of magnocellular cells and the plurality of non-magnocellular cells (blocked 236). The determined visual processing profile for the person may then be compared to a predetermined visual processing profile to determine a variance from a predetermined visual processing profile (block 240).

The predetermined visual processing profile may correspond to a person highly skilled in a particular physical activity based on a ratio of determined levels of retinal ganglion function for at least a first and second retinal ganglion subtypes for the person highly skilled in the particular physical activity. The highly skilled person could be, for example, a professional baseball player, a professional basketball player, a professional football player, a professional tennis player, a professional golfer, a professional race car driver, a member of the military, a member of law enforcement, etc. Or it could be used for a person with a disease process, where it is used to assist with a health improvement process or other therapeutic activities, etc. The predetermined visual processing profile may be calculated by accumulating visual processing profiles for a plurality of people, which could include a plurality of professionals within a professional sport and possibly within professionals having similar positions within the specific professional sport. For example, predetermined visual processing profiles could be created for professional baseball players in separate categories for batting and fielding.

While not shown, the method 200 could also include accumulating visual processing profiles for a plurality of people and further accumulating demographic data that corresponds to the visual processing profiles for each of the plurality of people, wherein the demographic data includes at least the sex and the age of each of the plurality of people. Once such a database is created, electronic advertisements can be created that are targeted to a group of people having at least one particular demographic attribute by causing the electronic advertisement to have a greater impact on the retino-geniculo-cortical pathway of the targeted group.

It should also be noted that the method 200 could alternatively display visual stimuli to other parts of the person's field of view in addition to those described above, or in place of those described above. For example, the method could also display and measure stimuli in a third portion of the person's field of view. It is also possible at the method 200 could incorporate the use of additional neutral density filters to further increase the accuracy of the visual processing profile developed for the person. Alternatively, fewer neutral density filters could be used to determine the person's visual processing profile, or even a completely different technology could be used to measure the levels of retinal ganglion function of the retinal ganglion subtypes when determining the visual processing profile. One example is discussed immediately below.

Figure 4:
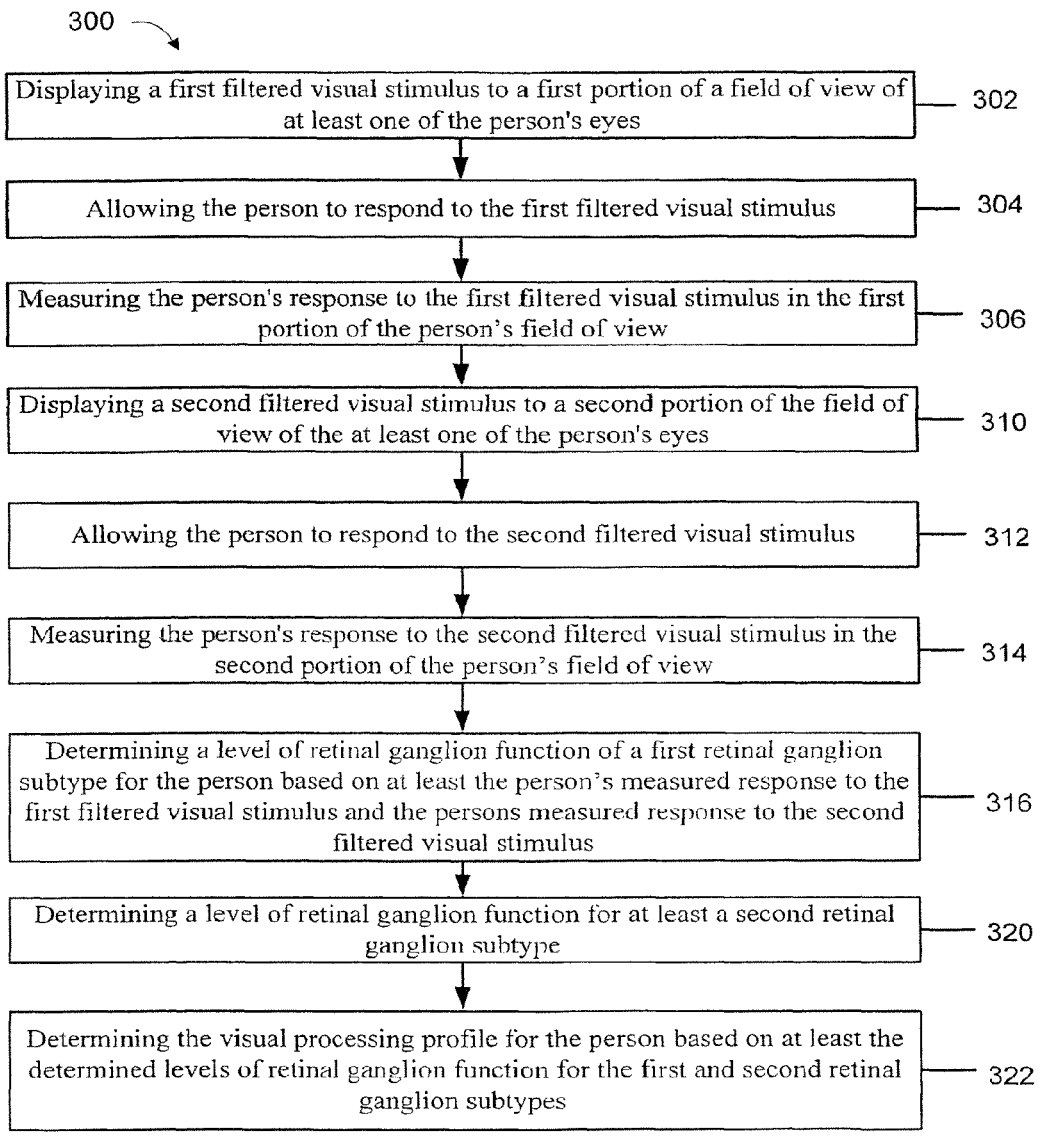
FIG. 4 is a flowchart describing another exemplary method of developing a visual processing profile.

FIG. 4 is an exemplary flowchart of an alternative method 300 of developing a visual processing profile. The method 300 may begin by displaying a first filtered visual stimulus to a first portion of a field of view of at least one of the person's eyes (block 302) and allow the person to respond to the filtered visual stimulus (block 304). The method may then measure a person's response to the first filtered visual stimulus in the first portion of the person's field of view (block 306), display a second filtered visual stimulus to a second portion of the field of view of the at least one of the person's eyes (block 310), and allow the person to respond to the second filtered visual stimulus (block 312).

The method 300 may then measure the person's response to at least the second filtered visual stimulus in at least the second portion of the person's field of view (block 314) and determine a level of retinal ganglion function of at least a first retinal ganglion subtype for the person based on at least the person's measured response to the first filtered visual stimulus and the person's measured response to the second filtered visual stimulus (block 316). The method may then determined a level of retinal ganglion function for at least a second retinal ganglion subtype (block 320) and determine the visual processing profile for the person based on at least the determined levels of retinal ganglion function for at least the first and second retinal ganglion subtypes (block 322).

The determination of a visual profile based on levels of performance may be useful as a diagnostic tool in assessing ability to perform as well as the modification necessary to increase performance. Thus, visual processing profiles could be used, for example, in a career counseling, in assisting patients with health related problems, and identifying people with particular genetic aptitudes (those with eyes having retino-geniculo-cortical pathways capable of providing a competitive advantage), in drafting professional athletes, etc.

In a study performed by testing the visual acuity of athletes with varying performance levels, an association between athletic performance and visual processing associated with particular retinal ganglion cells types was shown. The study focused on baseball players having varying batting averages (BA) and assists. Table 1 shows the results of the study. Visual processing in individuals was measured using the FDT techniques to detect m-cell function. As described in Table 1 below, athletes having an increased batting average showed depression of m-cell function in central middle and peripheral visual fields which is interpreted as an increase in p and k cell function. On the other hand, athletes having lower batting averages showed varying m-cell function in the visual fields. Furthermore, players having higher assists (better fielders) showed increased m-cell function. Neutral density filters were utilized having 0.3 and 0.6 filter densities.

by comparing the level of retinal ganglion function measured to a predetermined level of function.

Once a visual profile is assessed, a visual stimulus is designed to alter processing in at least one retinal ganglion cell type. A means for determining stimulus in response to the level of visual functions associated with at least one cell type may be devised. As will be described in detail below, a visual stimulus may be designed to activate, reduce or terminate function in a particular retinal ganglion cell type based on its associated visual function. Such visual stimulus may be focused to affect conduction velocity, receptive fields, electrical potential rates in other retinal neurons, and action potential rates in retinal ganglion cells. By providing a stimulus that affects the retino-geniculo-cortical pathways in response to the level of function, visual acuity may be altered.

Generally, the visual stimulus is provided to an individual in need of visual modification. The visual stimulus is provided by various means including, but not limited to, computer games, video games, board games, or other software tools. In certain embodiments, the visual stimulus is stored and/or displayed in a variety of means known in the art where a user may access the stimulus.

In some embodiments, a visual stimulus is determined to modify function in at least one type of retinal ganglion cell based on the function associated with the cell type. For example, the p-cell and/or k-cell pathways may be stimulated based on association with color sensitivity. As described above, p-cells and k-cells are associated with the red-green and yellow-blue color opponencies, respectively. Thus, a means is provided for determining and/or altering the ratio of p and k-cell function based on stimulation of color opponency pathways.

P-cells mediate red-green color vision via detection of a difference in L and M cone cells. Thus, a red-green system is created to address a low ratio of p-cell function in an individual. In one example, a red stimulus is presented on a green background, or vice versa, and presented to an individual to increase the ratio of p-cell function. Similarly, a blue-yellow system is created to modify the ratio of k-cell function.

TABLE 1

Association Between Batting Statistic and Visual Field Acuity in Baseball Players

| Player | Batting Average | Assist | 0.3 Filter Peripheral Boxes | 0.3 Filter Center Boxes | 0.3 Filter Middle Circle | 0.6 Filter Peripheral Boxes | 0.6 Filter Center Boxes | 0.6 Filter Middle Circle |
|---|---|---|---|---|---|---|---|---|
| 1 | 0.352 | 74 | 18 | 12 | 0 | 35 | 39 | 20 |
| 2 | 0.000 | 0 | 11 | 6 | 10 | 12 | 6 | 10 |
| 3 | 0.316 | 0 | 0 | 0 | 0 | 11 | 0 | 0 |
| 4 | 0.342 | 72 | 8 | 3 | 0 | 16 | 12 | 5 |
| 5 | 0.000 | 0 | 2 | 0 | 5 | 5 | 3 | 0 |
| 6 | 0.288 | 155 | 0 | 0 | 0 | 1 | 0 | 0 |
| 7 | 0.326 | 139 | 13 | 3 | 10 | 25 | 12 | 5 |
| 8 | 0.285 | 125 | 0 | 0 | 0 | 2 | 0 | 0 |

Comparison of the visual profile to the predetermined visual profile provides a level of variance in retinal ganglion subtype cell function. As discussed below, the measured variance may be addressed by creating or generating a visual stimulus to increase or decrease retinal ganglion function, thereby diminishing the variance.

In one instance, a visual profile may be used to address aberrant visual function. The determination of aberrant function may be based on a number of indicia relating to the specific type of visual processing desired by or lacking in an individual. In one example, aberrant function is determined Such systems were tested to determine efficacy in altering visual processing in individuals. Table 2 below shows the differences between retinal ganglion function before and after such stimulus was presented to the individuals. The Tbase mean batting average was determined by assessing visual processing in ten individuals prior to stimulation. Subsequently, those individuals were exposed to stimulation in accordance with the present invention for a time interval of seven minutes. After seven minutes elapsed, the Tseven mean batting average was calculated by assessing visual processing in the ten individuals following stimulation. The statistical significance of the alteration in visual processing following seven minutes of stimulation is shown in Table 3 below, which means that the statistical significance in the improved batting averages was obtained with a P value of less than 0.01 (0.006 actual) confidence level of 99%.

TABLE 2

Paired Samples Statistics

|  | Mean | N | Std. Deviation | Std. Error Mean |
|---|---|---|---|---|
| Tbase | .6300 | 10 | .16700 | .05281 |
| Tseven | .770 | 10 | .15129 | .04784 |

TABLE 3

Association Between Stimulus and Improvement in Visual Processing
Paired Samples Test

| | Paired Differences | | | | | | | |
|---|---|---|---|---|---|---|---|---|
| | | | Std. Error | 95% Confidence Interval of the Difference | | | | |
| | Mean | Std. Deviation | Mean | Lower | Upper | t | df | Sig. (2-tailed) |
| Pair 1 Tbase - Tseven | −.14000 | .12428 | .03930 | −.22890 | −.05110 | −3.562 | 9 | .006 |

Thus, providing a stimulus in accordance with the present disclosure causes a significant alteration in visual processing. In certain aspects, the stimulus color combines with the background color progressively in response to successful visual performance.

M-cells do not show association with chromatic stimulus, thus, an achromatic system of stimulus may be used to determine and modify the ratio of functioning m-cells. The methods and systems of the present disclosure are useful in determination and alteration of retinal ganglion function in adults and children.

Figure 5:
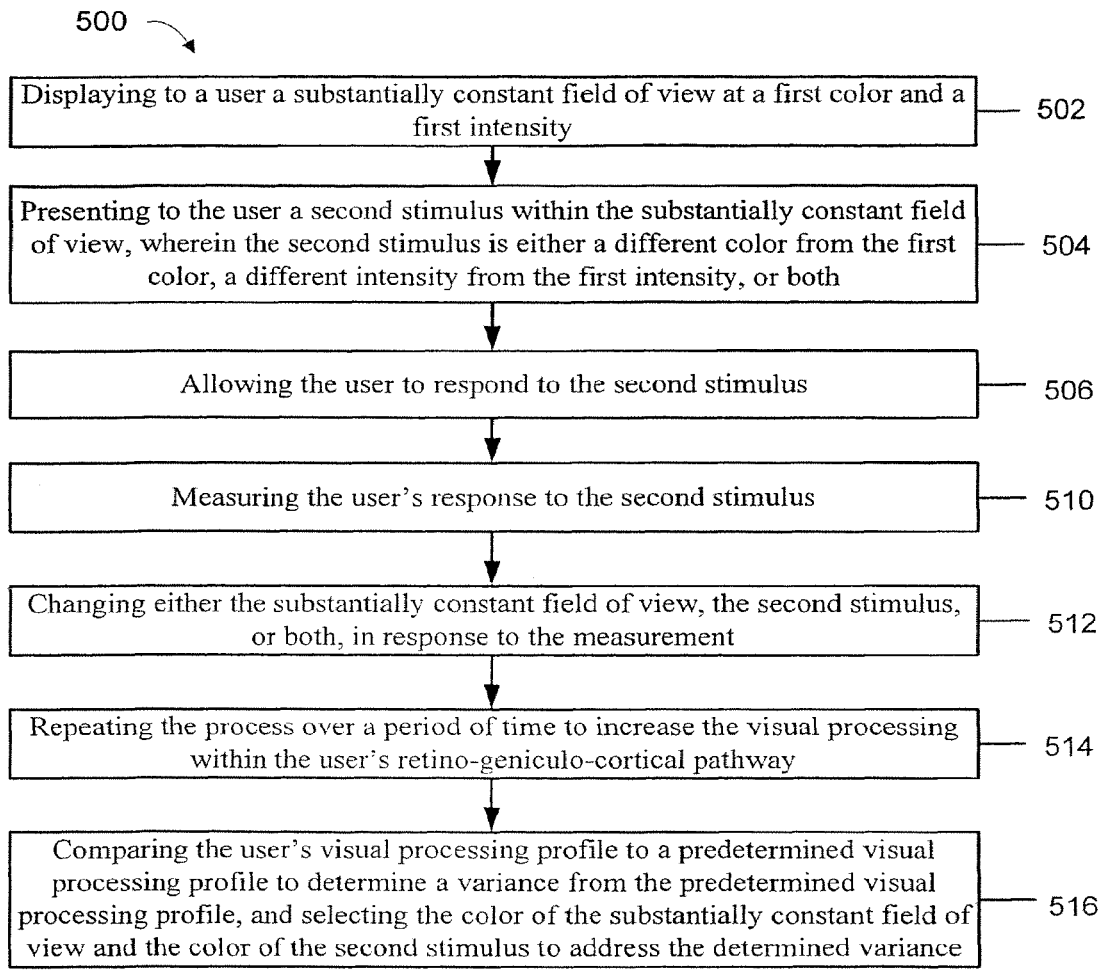
FIG. 5 is a flowchart describing a method of one example of enhancing a retino-geniculo-cortical pathway for a particular activity.

FIG. 5 illustrates an exemplary flowchart 500 of enhancing a retino-geniculo-cortical pathway for a particular activity. The method 500 may begin by displaying to a user a substantially constant field of view at a first color (i.e. wavelength) and a first intensity (block 502) and present to the user a second stimulus within the substantially constant field of view, wherein the second stimulus is either a different color from the first color, a different intensity from the first intensity, or both (block 504). The second stimulus may model a movement of an object toward a user. The method may also include allowing the user to respond to the second stimulus (block 506), measuring the user's response to the second stimulus (block 510), and changing either the substantially constant field of view, the second stimulus, or both, in response to the measurement (block 512). The method may change the second stimulus by either decreasing or increasing the intensity of the second stimulus, or by changing the color of the second stimulus, or both. It is possible that the change to either the constant field of view, the second stimulus, or both, may be performed in real time in response to the measurements.

The method 500 may then repeat the process over a period of time to increase the visual processing within the user's retino-geniculo-cortical pathway (block 514). This process may be repeated for about five to ten minutes, or for approximately seven minutes. However, alternative lengths of time may be used within a particular system. The method may then compare the user's visual processing profile to a predetermined visual processing profile to determine a variance from the predetermined visual processing profile, and select the color of the substantially constant field of view and the color of the second stimulus to address the determined variance (block 516).

The color of the substantially constant field of view and the color of the second stimulus may be selected based on a visual processing profile previously determined for the user. In other words, the color of the substantially constant field of view and the color of the second stimulus may be selected based on a ratio of levels of retinal ganglion function for a plurality of magnocellular cells and a plurality of non-magnocellular cells. Thus, increasing the visual processing within the user's retino-geniculo-cortical pathway involves increasing the user's visual processing in at least one subtype of the user's retinal ganglion cells.

While not shown in FIG. 5, the method of 500 may include varying the degree of changes based on the measured responses. For example, the intensity of the second stimulus may be decreased at a greater rate if the user's measured responses are exceedingly accurate. Likewise, the intensity of the second stimulus may be decreased at a slower rate, or even increased, if the user's measured responses become worse (i.e., the user fails to see the second stimulus or fails to see the second stimulus in time to generate an appropriate response).

The method of 500 may also adjust the presentation to the user of the second stimulus by adjusting the position of the second stimulus within the substantially constant field of view. This adjustment may be performed automatically based on a specific enhancement identified by the user. For example, the user could indicate that he wishes to work on and enhance a specific area of ganglion cells by repeatedly responding to retino-geniculo-cortical pathway stimulation in a specific quadrant of the user's field of view.

After repeating the process over a period of time, the user may then perform the actual physical activity within a set period time, and will likely see a marked improvement in his or her performance.

Figure 6:
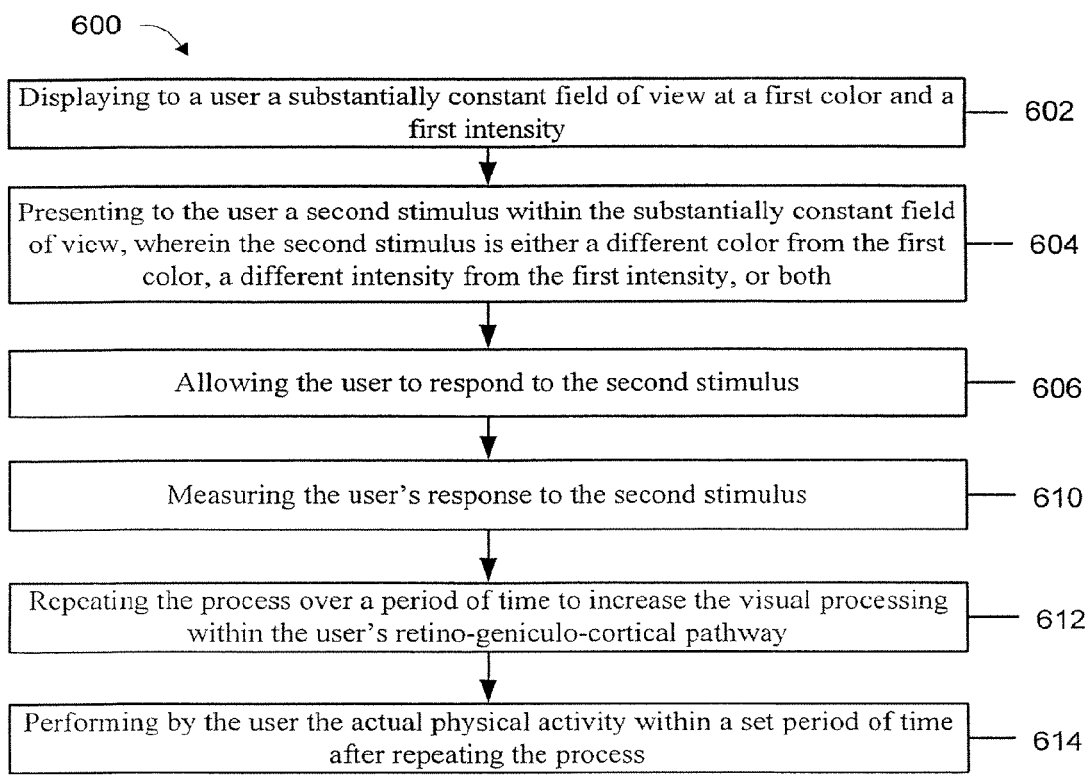
FIG. 6 is a flowchart describing another exemplary method of enhancing a retino-geniculo-cortical pathway for a particular activity.

FIG. 6 illustrates an exemplary alternative flowchart 600 of enhancing a retino-geniculo-cortical pathway for a particular activity. The method 600 may begin by displaying to a user a substantially constant field of view at a first color (i.e. wavelength) and a first intensity (block 602) and present to the user a second stimulus within the substantially constant field of view, wherein the second stimulus is either a different color from the first color, a different intensity from the first intensity, or both (block 604). The method may also include allowing the user to respond to the second stimulus (block 606) and measuring the user's response to the second stimulus (block 610).

The method 600 may then repeat the process over a period of time to increase the visual processing within the user's retino-geniculo-cortical pathway (block 614). Thereafter, the user may then perform the actual physical activity within a set period time.

Figure 7:
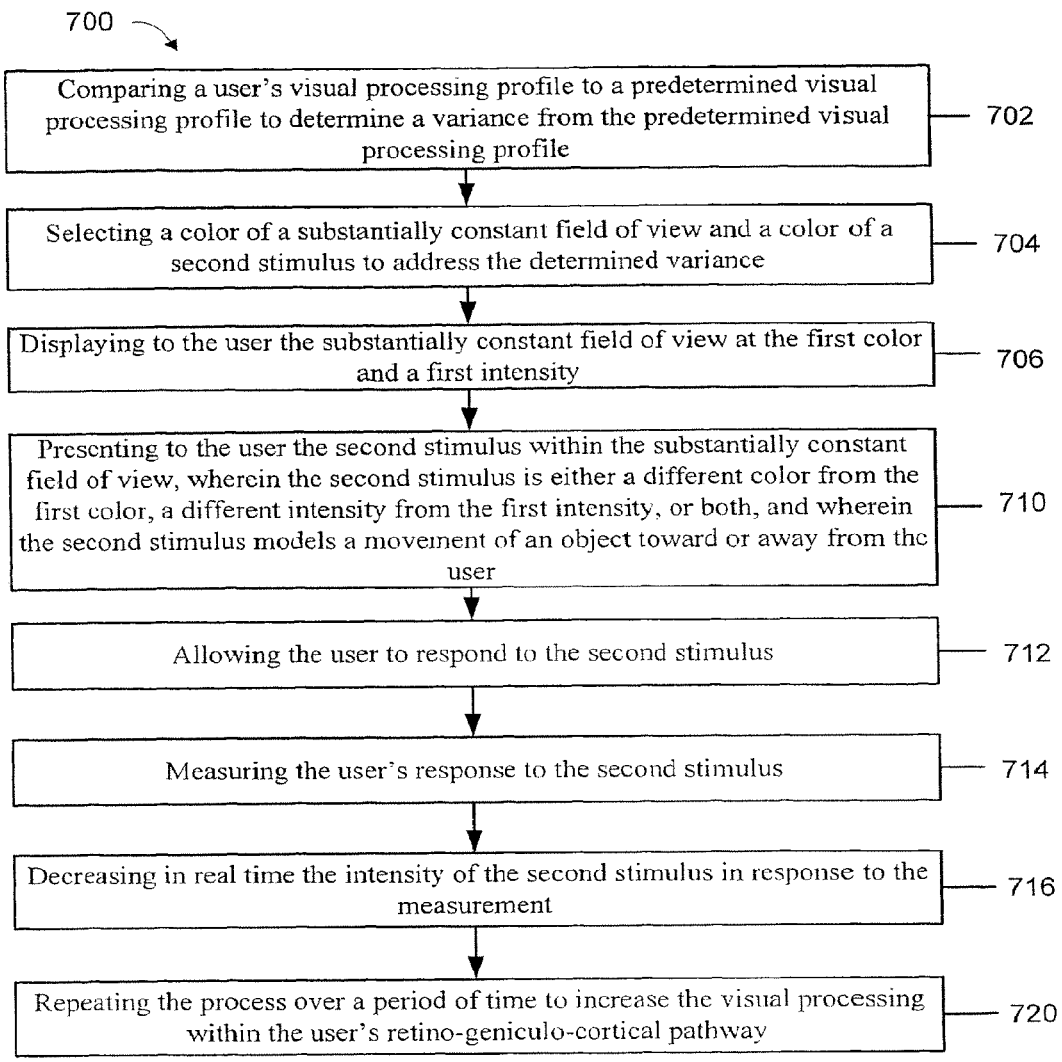
FIG. 7 is a flowchart describing another exemplary method of enhancing a retino-geniculo-cortical pathway for a particular activity.

FIG. 7 illustrates a flowchart 700 illustrating another exemplary method of enhancing a retino-geniculo-cortical pathway for a particular activity. The method 700 may begin by comparing a user's visual processing profile to a predetermined visual processing profile to determine a variance from the predetermined visual processing profile (block 702) and selecting a color of a substantially constant field of view and a color of a second stimulus to address the determined variance (block 704). The method may then display to the user to substantially constant field of view at the first color and a first intensity (block 706) and present to the user the second stimulus within the substantially constant field of view, wherein the second stimulus is either a different color from the first color, a different intensity from the first intensity, or both, and wherein the second stimulus models a movement of an object toward or away from the user (block 710).

The method 700 may then allow the user to respond to the second stimulus (block 712), measure the user's response to the second stimulus (block 714), decrease in real-time the intensity of the second stimulus and response to the measurement (block 716), and repeat the process over a period of time to increase the visual processing within the user's retino-geniculo-cortical pathway (block 720).

The disclosure is based on determination and alteration of visual profiles based on levels of retinal ganglion cell function. The disclosed methods are designed to stimulate visual pathways associated with one or more specific retinal ganglion cell types, thereby altering the ratio of function in these retinal ganglion cell types. Thus, the disclosed methods may be used to diagnose, develop and alter visual profiles based on the function of at least one type of retinal ganglion cell.

Although the forgoing text sets forth a detailed description of numerous different embodiments, it should be understood that the scope of the patent is defined by the words of the claims set forth at the end of this patent. The detailed description is to be construed as exemplary only and does not describe every possible embodiment because describing every possible embodiment would be impractical, if not impossible. Numerous alternative embodiments could be implemented, using either current technology or technology developed after the filing date of this patent, which would still fall within the scope of the claims.

Thus, many modifications and variations may be made in the techniques and structures described and illustrated herein without departing from the spirit and scope of the present claims. Accordingly, it should be understood that the methods and apparatus described herein are illustrative only and are not limiting upon the scope of the claims.

The invention claimed is:

1. A method of developing a visual processing profile for a person, comprising:
    displaying a first filtered visual stimulus to a first portion of a field of view of at least one of the person's eyes;
    allowing the person to respond to the first filtered visual stimulus;
    measuring the person's response to the first filtered visual stimulus in the first portion of the person's field of view;
    displaying a second filtered visual stimulus to a second portion of the field of view of the at least one of the person's eyes;
    allowing the person to respond to the second filtered visual stimulus;
    measuring the person's response to the second filtered visual stimulus in the second portion of the person's field of view;
    determining a level of retinal ganglion function of a first retinal ganglion subtype for the person based on at least the person's measured response to the first filtered visual stimulus and the persons measured response to the second filtered visual stimulus;
    determining a level of retinal ganglion function for at least a second retinal ganglion subtype; and
    determining the visual processing profile for the person based on at least the determined levels of retinal ganglion function for at least the first and second retinal ganglion subtypes.

2. The method of claim 1, further comprising comparing the determined visual processing profile for the person to a predetermined visual processing profile to determine a variance from the predetermined visual processing profile.

3. The method of claim 2, wherein the predetermined visual processing profile is obtained by determining a visual processing profile for a person highly skilled in a particular physical activity based on a ratio of determined levels of retinal ganglion function for at least a first and second retinal ganglion subtypes for the person highly skilled in the particular physical activity.

4. The method of claim 1, wherein displaying the first and second filtered visual stimuli comprises filtering the first stimulus and second stimulus with a neutral density filter.

5. The method of claim 4, further comprising displaying a third filtered visual stimulus to the first portion of the field of view using a second, darker neutral density filter;
    allowing the person to respond to the third filtered visual stimulus;
    measuring the person's response to the third filtered visual stimulus in the first portion of the person's field of view;
    displaying a fourth filtered visual stimulus to the second portion of the field of view using the second, darker neutral density filter;
    allowing the person to respond to the fourth filtered visual stimulus;
    measuring the person's response to the fourth filtered visual stimulus in the second portion of the person's field of view;
    determining the level of retinal ganglion function of the retinal ganglion subtype for the person based on the person's measured responses to at least the first, second, third, and fourth filtered visual stimuli;
    determining the level of retinal ganglion function for the second retinal ganglion subtype; and
    determining the visual processing profile for the person based on a ratio of the determined levels of retinal ganglion function for at least the first and second retinal ganglion subtypes.

6. The method of claim 1, wherein determining the level of retinal ganglion function for the first subtype comprises determining a level of retinal ganglion function for the person's magnocellular cells; and
    wherein determining the level of retinal ganglion function for at least the second subtype comprises determining a level of retinal ganglion function for the person's parvocellular cells.

7. The method of claim 6, further comprising determining a level of retinal ganglion function for the person's koniocellular cells.

8. The method of claim 1, wherein displaying the first filtered visual stimulus to the first portion of the field of view comprises displaying the first visual stimulus to one of a central superior portion, a central nasal portion, a central inferior portion, a central temporal portion, a peripheral superior portion, a peripheral nasal portion, a peripheral inferior portion, a peripheral temporal portion, or the entire field of view.

9. The method of claim 8, further comprising displaying a third filtered visual stimulus to a third portion of the field of view.

10. The method of claim 1, wherein displaying the first and second visual stimuli and measuring the person's response to the first and second visual stimuli are performed using a frequency doubling technology.

11. The method of claim 1, further comprising accumulating visual processing profiles for a plurality of people and further accumulating demographic data that corresponds to the visual processing profiles for each of the plurality of people, wherein the demographic data includes at least the sex and the age of each of the plurality of people.

12. The method of claim 11, further comprising creating an electronic advertisement targeted to a group of people having at least one particular demographic attribute by causing the electronic advertisement to have a greater impact on the retino-geniculo-cortical pathway of the targeted group.

13. A method of developing a visual processing profile for a person, comprising:
    displaying a first filtered visual stimulus to a first portion of the person's field of view using a neutral density filter;
    allowing the person to respond to the first filtered visual stimulus;
    measuring the person's response to the first filtered visual stimulus in the first portion of the person's field of view;
    displaying a second filtered visual stimulus to a second portion of the person's field of view;
    allowing the person to respond to the second filtered visual stimulus;
    measuring the person's response to the second filtered visual stimulus in the second portion of the person's field of view;
    determining a level of retinal ganglion function of a plurality of magnocellular cells for the person based on at least the person's measured response to at least the first filtered visual stimulus and the persons measured response to the second filtered visual stimulus;
    determining a level of retinal ganglion function for a plurality of non-magnocellular cells; and
    determining the visual processing profile for the person based on at least the determined levels of retinal ganglion function for at least the plurality of magnocellular cells and the plurality of non-magnocellular cells.

14. The method of claim 13, further comprising comparing the determined visual processing profile for the person to a predetermined visual processing profile to determine a variance from the predetermined visual processing profile.

15. The method of claim 14, wherein the predetermined visual processing profile is obtained by determining a visual processing profile for a person highly skilled in a particular physical activity based on a ratio of determined levels of retinal ganglion function for at least a first and second retinal ganglion subtypes for the person highly skilled in the particular physical activity.

16. The method of claim 13, further comprising displaying a third filtered visual stimulus to the first portion of the field of view using a second, darker neutral density filter;
    allowing the person to respond to the third filtered visual stimulus;
    measuring the person's response to the third filtered visual stimulus in the first portion of the person's field of view;
    displaying a fourth filtered visual stimulus to the second portion of the person's field of view using the second, darker neutral density filter;
    allowing the person to respond to the fourth filtered visual stimulus;
    measuring the person's response to the fourth filtered visual stimulus in the second portion of the person's field of view;
    determining the level of retinal ganglion function of the plurality of magnocellular cells based on the person's measured responses to at least the first, second, third, and fourth filtered visual stimuli;
    determining the level of retinal ganglion function for the plurality of non-magnocellular cells; and
    determining the visual processing profile for the person based on a ratio of the determined levels of retinal ganglion function for at least the plurality of magnocellular cells and the plurality of non-magnocellular cells.

17. The method of claim 16, further comprising displaying the third filtered visual stimulus to a temporal portion of the field of view.

* * * * *